United States Patent
Zhou (10) Patent No.: US 8,251,976 B2
(45) Date of Patent: Aug. 28, 2012

(54) MEDICAL DEVICE INCORPORATING A POLYMER BLEND

(75) Inventor: Pu Zhou, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 323 days.

(21) Appl. No.: 12/606,488

(22) Filed: Oct. 27, 2009

(65) Prior Publication Data

US 2010/0043959 A1  Feb. 25, 2010

Related U.S. Application Data

(63) Continuation of application No. 10/875,108, filed on Jun. 23, 2004, now Pat. No. 7,615,043, which is a continuation-in-part of application No. 10/645,764, filed on Aug. 20, 2003, now Pat. No. 7,824,392.

(51) Int. Cl.
*A61M 25/00* (2006.01)

(52) U.S. Cl. .................................. 604/523; 264/171.12

(58) Field of Classification Search .......... 604/523–524; 606/191–194; 264/164–171.12
See application file for complete search history.

(56) References Cited

U.S. PATENT DOCUMENTS

| | | |
|---|---|---|
| 2,437,542 A | 3/1948 | Krippendorf |
| 2,472,483 A | 6/1949 | Krippendorf |
| 2,472,484 A | 6/1949 | Krippendorf |
| 2,472,485 A | 6/1949 | Krippendorf |
| 3,416,531 A | 12/1968 | Edwards |
| 3,463,197 A | 8/1969 | Slade |
| 3,481,368 A | 12/1969 | Vansickle et al. |
| 3,485,234 A | 12/1969 | Stevens |
| 3,612,058 A | 10/1971 | Ackerman |
| 3,924,632 A | 12/1975 | Cook |
| 4,210,478 A | 7/1980 | Shoney |
| 4,279,252 A | 7/1981 | Martin |
| 4,321,226 A | 3/1982 | Markling |
| 4,385,635 A | 5/1983 | Ruiz |
| 4,419,095 A | 12/1983 | Nebergall et al. |

(Continued)

FOREIGN PATENT DOCUMENTS

EP  0 180 348 B1  5/1986

(Continued)

OTHER PUBLICATIONS

Ahmed, Salmaan et al., "Magnetic Resonance Imaging Safety: Implications for Cardiovascular Patients," *Journal of Cardiovascular Magnetic Resonance*, vol. 3, No. 3 (2001), pp. 171-182.

(Continued)

*Primary Examiner* — Manuel Mendez
(74) *Attorney, Agent, or Firm* — Seager, Tufte & Wickhem, LLC (57) ABSTRACT

A catheter including a catheter shaft formed from a polymer blend and/or a braid. The polymer blend may include polyoxymethylene added in the dispersion phase to a polymer blend. The catheter braid can be formed from at least two continuous wires that are woven together. The catheter braid can include a proximal braid section and a distal braid section. Each of the continuous wires has a proximal diameter corresponding to the proximal braid section and a distal diameter corresponding to the distal braid section. The distal diameter of each wire can be less than the proximal diameter of that wire. A catheter braid so formed can be included in a catheter.

9 Claims, 5 Drawing Sheets

U.S. PATENT DOCUMENTS

| | | | |
|---|---|---|---|
| 4,425,919 A | 1/1984 | Alston, Jr. et al. | |
| 4,430,083 A | 2/1984 | Ganz et al. | |
| 4,447,239 A | 5/1984 | Krütten | |
| 4,484,586 A | 11/1984 | McMickle et al. | |
| 4,495,134 A | 1/1985 | Ouchi et al. | |
| 4,516,970 A | 5/1985 | Kaufman et al. | |
| 4,516,972 A | 5/1985 | Samson | |
| 4,531,943 A | 7/1985 | Van Tassel et al. | |
| 4,563,181 A | 1/1986 | Wijayarathna et al. | |
| 4,571,240 A | 2/1986 | Samson et al. | |
| 4,577,543 A | 3/1986 | Wilson | |
| 4,588,399 A | 5/1986 | Nebergall et al. | |
| 4,636,346 A | 1/1987 | Gold et al. | |
| 4,639,252 A | 1/1987 | Kelly et al. | |
| 4,657,024 A | 4/1987 | Coneys | |
| 4,665,604 A | 5/1987 | Dubowik | |
| 4,690,175 A | 9/1987 | Ouchi et al. | |
| 4,705,511 A | 11/1987 | Kocak | |
| 4,735,620 A | 4/1988 | Ruiz | |
| 4,737,153 A | 4/1988 | Shimamura et al. | |
| 4,764,324 A | 8/1988 | Burnham | |
| 4,817,613 A | 4/1989 | Jaraczewski et al. | |
| 4,838,879 A | 6/1989 | Tanabe et al. | |
| 4,842,590 A | 6/1989 | Tanabe et al. | |
| 4,863,442 A | 9/1989 | DeMello et al. | |
| 4,898,591 A | 2/1990 | Jang et al. | |
| 4,899,787 A | 2/1990 | Ouchi et al. | |
| 4,904,431 A | 2/1990 | O'Maleki | |
| 4,981,478 A | 1/1991 | Evard et al. | |
| 4,985,022 A | 1/1991 | Fearnot et al. | |
| 5,017,259 A | 5/1991 | Kohsai | |
| 5,019,057 A | 5/1991 | Truckai | |
| 5,037,404 A | 8/1991 | Gold et al. | |
| 5,045,072 A | 9/1991 | Castillo et al. | |
| 5,057,092 A | 10/1991 | Webster, Jr. | |
| 5,069,674 A | 12/1991 | Fearnot et al. | |
| 5,078,702 A | 1/1992 | Pomeranz | |
| 5,160,559 A | 11/1992 | Scovil et al. | |
| 5,163,431 A | 11/1992 | Griep | |
| 5,176,660 A | 1/1993 | Truckai | |
| 5,178,158 A | 1/1993 | de Toledo | |
| 5,180,376 A | 1/1993 | Fischell | |
| 5,184,627 A | 2/1993 | de Toledo | |
| 5,190,520 A | 3/1993 | Fenton, Jr. et al. | |
| 5,217,440 A | 6/1993 | Frassica | |
| 5,217,482 A | 6/1993 | Keith | |
| 5,218,037 A * | 6/1993 | Orikasa et al. | 524/504 |
| 5,219,335 A | 6/1993 | Willard et al. | |
| 5,221,270 A | 6/1993 | Parker | |
| 5,221,372 A | 6/1993 | Olson | |
| 5,222,949 A | 6/1993 | Kaldany | |
| 5,226,899 A | 7/1993 | Lee et al. | |
| 5,234,416 A | 8/1993 | Macaulay et al. | |
| 5,248,305 A | 9/1993 | Zdrahala | |
| 5,254,107 A | 10/1993 | Soltesz | |
| 5,258,160 A | 11/1993 | Utsumi et al. | |
| 5,279,596 A | 1/1994 | Castaneda et al. | |
| 5,306,252 A | 4/1994 | Yuteri et al. | |
| 5,308,342 A | 5/1994 | Sepetka et al. | |
| 5,318,032 A | 6/1994 | Lonsbury et al. | |
| 5,334,169 A | 8/1994 | Brown et al. | |
| 5,335,305 A | 8/1994 | Kosa et al. | |
| 5,353,808 A | 10/1994 | Viera | |
| 5,358,493 A | 10/1994 | Schweich, Jr. et al. | |
| 5,403,292 A | 4/1995 | Ju | |
| 5,417,981 A | 5/1995 | Endo et al. | |
| 5,423,773 A | 6/1995 | Jimenez | |
| 5,423,774 A | 6/1995 | Fischell et al. | |
| 5,441,489 A | 8/1995 | Utsumi et al. | |
| 5,445,624 A | 8/1995 | Jimenez | |
| 5,451,209 A | 9/1995 | Ainsworth et al. | |
| 5,453,099 A | 9/1995 | Lee et al. | |
| 5,454,795 A | 10/1995 | Samson | |
| 5,484,565 A * | 1/1996 | Larsen et al. | 264/230 |
| 5,496,294 A | 3/1996 | Hergenrother et al. | |
| 5,499,973 A | 3/1996 | Saab | |
| 5,509,910 A | 4/1996 | Lunn | |
| 5,514,108 A | 5/1996 | Stevens | |
| 5,531,721 A | 7/1996 | Pepin et al. | |
| 5,533,987 A | 7/1996 | Pray et al. | |
| 5,538,513 A | 7/1996 | Okajima | |
| 5,545,151 A | 8/1996 | O'Connor et al. | |
| 5,554,139 A | 9/1996 | Okajima | |
| 5,569,218 A | 10/1996 | Berg | |
| 5,569,220 A | 10/1996 | Webster, Jr. | |
| 5,584,821 A | 12/1996 | Hobbs et al. | |
| 5,599,319 A | 2/1997 | Stevens | |
| 5,599,326 A | 2/1997 | Carter | |
| 5,603,705 A | 2/1997 | Berg | |
| 5,624,617 A | 4/1997 | Sorabella et al. | |
| 5,639,409 A | 6/1997 | van Muiden | |
| 5,658,263 A | 8/1997 | Dang et al. | |
| 5,658,264 A | 8/1997 | Samson | |
| 5,662,622 A | 9/1997 | Gore et al. | |
| 5,664,580 A | 9/1997 | Erickson et al. | |
| 5,667,499 A | 9/1997 | Welch et al. | |
| 5,674,208 A | 10/1997 | Berg et al. | |
| 5,676,659 A | 10/1997 | McGurk | |
| 5,695,483 A | 12/1997 | Samson | |
| 5,702,373 A | 12/1997 | Samson | |
| 5,711,909 A | 1/1998 | Gore et al. | |
| 5,725,513 A | 3/1998 | Ju et al. | |
| 5,728,079 A | 3/1998 | Weber et al. | |
| 5,730,733 A | 3/1998 | Mortier et al. | |
| 5,738,742 A | 4/1998 | Stevens | |
| 5,755,704 A | 5/1998 | Lunn | |
| 5,772,609 A | 6/1998 | Nguyen et al. | |
| 5,782,809 A | 7/1998 | Umeno et al. | |
| 5,782,811 A * | 7/1998 | Samson et al. | 604/527 |
| 5,792,124 A | 8/1998 | Horrigan et al. | |
| 5,795,341 A | 8/1998 | Samson | |
| 5,827,242 A | 10/1998 | Follmer et al. | |
| 5,836,926 A | 11/1998 | Peterson et al. | |
| 5,876,386 A | 3/1999 | Samson | |
| 5,885,207 A | 3/1999 | Iwasaka | |
| 5,891,112 A | 4/1999 | Samson | |
| 5,891,114 A | 4/1999 | Chien et al. | |
| 5,899,892 A | 5/1999 | Mortier et al. | |
| 5,906,605 A | 5/1999 | Coxum | |
| 5,906,606 A | 5/1999 | Chee et al. | |
| 5,911,715 A | 6/1999 | Berg et al. | |
| 5,938,653 A | 8/1999 | Pepin | |
| 5,947,925 A | 9/1999 | Ashiya et al. | |
| 5,947,939 A | 9/1999 | Mortier et al. | |
| 5,947,940 A | 9/1999 | Beisel | |
| 5,951,539 A | 9/1999 | Nita et al. | |
| 5,964,971 A | 10/1999 | Lunn | |
| 5,972,143 A | 10/1999 | Stevens | |
| 6,042,578 A | 3/2000 | Dinh et al. | |
| 6,045,734 A | 4/2000 | Luther et al. | |
| 6,053,904 A | 4/2000 | Scribner et al. | |
| 6,090,099 A | 7/2000 | Samson et al. | |
| 6,099,499 A | 8/2000 | Ciamacco, Jr. | |
| 6,099,561 A | 8/2000 | Alt | |
| 6,102,890 A | 8/2000 | Stivland et al. | |
| 6,113,579 A | 9/2000 | Eidenschink et al. | |
| 6,139,510 A | 10/2000 | Palermo | |
| 6,143,013 A | 11/2000 | Samson et al. | |
| 6,152,911 A | 11/2000 | Giannoble | |
| 6,152,912 A | 11/2000 | Jansen et al. | |
| 6,159,187 A | 12/2000 | Park et al. | |
| 6,165,163 A | 12/2000 | Chien et al. | |
| 6,171,295 B1 | 1/2001 | Garabedian et al. | |
| 6,186,978 B1 | 2/2001 | Samson et al. | |
| 6,197,014 B1 | 3/2001 | Samson et al. | |
| 6,212,422 B1 | 4/2001 | Berg et al. | |
| 6,217,565 B1 | 4/2001 | Cohen | |
| 6,245,068 B1 | 6/2001 | Olson et al. | |
| 6,251,092 B1 | 6/2001 | Qin et al. | |
| 6,258,080 B1 | 7/2001 | Samson | |
| 6,284,333 B1 | 9/2001 | Wang et al. | |
| 6,290,692 B1 | 9/2001 | Klima et al. | |
| 6,296,631 B2 | 10/2001 | Chow | |
| 6,315,757 B1 | 11/2001 | Chee et al. | |
| 6,322,534 B1 | 11/2001 | Shkolnik | |
| 6,355,027 B1 | 3/2002 | Le et al. | |
| 6,358,238 B1 | 3/2002 | Sherry | |

| | | |
|---|---|---|
| 6,368,316 B1 | 4/2002 | Jansen et al. |
| 6,387,121 B1 | 5/2002 | Alt |
| 6,443,925 B1 | 9/2002 | Schaible et al. |
| 6,451,026 B1 | 9/2002 | Biagtan et al. |
| 6,458,867 B1 | 10/2002 | Wang et al. |
| 6,464,684 B1 | 10/2002 | Galdonik |
| 6,465,067 B1 | 10/2002 | Wang et al. |
| 6,485,457 B1 | 11/2002 | Hisamatsu et al. |
| 6,500,147 B2 | 12/2002 | Omaleki et al. |
| 6,503,353 B1 | 1/2003 | Peterson et al. |
| 6,508,804 B2 | 1/2003 | Sarge et al. |
| 6,508,805 B1 | 1/2003 | Garabedian et al. |
| 6,511,462 B1 | 1/2003 | Itou et al. |
| 6,540,743 B2 | 4/2003 | Olson et al. |
| 6,562,022 B2 | 5/2003 | Hoste et al. |
| 6,575,958 B1 | 6/2003 | Happ et al. |
| 6,635,047 B2 | 10/2003 | Forsberg |
| 6,648,854 B1 | 11/2003 | Patterson et al. |
| 6,669,886 B1 | 12/2003 | Willard |
| 6,709,429 B1 | 3/2004 | Schaefer et al. |
| 7,112,298 B2 | 9/2006 | Kampa et al. |
| 2003/0009184 A1 | 1/2003 | Pepin |
| 2003/0055402 A1 | 3/2003 | Zhou |
| 2003/0135114 A1 | 7/2003 | Pacetti et al. |
| 2003/0167051 A1 | 9/2003 | Zhou |
| 2005/0043713 A1 | 2/2005 | Zhou |

FOREIGN PATENT DOCUMENTS

| | | |
|---|---|---|
| EP | 0 277 366 A1 | 8/1988 |
| EP | 0 382 974 A1 | 8/1990 |
| EP | 0 473 045 A1 | 8/1990 |
| EP | 0 555 088 A2 | 8/1993 |
| EP | 0 732 117 A2 | 9/1996 |
| EP | 0 810 003 A2 | 12/1997 |
| WO | WO 92/15356 A1 | 9/1992 |
| WO | WO 96/33763 A2 | 10/1996 |
| WO | WO 98/50097 A1 | 11/1998 |
| WO | WO 00/43061 A1 | 7/2000 |
| WO | WO 01/10492 A1 | 2/2001 |
| WO | WO 01/54761 A2 | 8/2001 |
| WO | WO 03/028783 A1 | 4/2003 |

OTHER PUBLICATIONS

Aleksandrovic, Vesna et al, "Synthesis and Characterization of Thermoplastic Copolyester Elastomers Modified with Fumaric Moieties," *J. Serb. Chem. Soc.*, vol. 66, No. 3 (2001) pp. 139-152.

Brochure—"Arnitel® Copolyester Elastomers, General Information on Applications and Properties," © Jun. 2001 DMS Engineering Plastics, 24 pages.

Brochure—"Arnitel® Copolyester Elastomers, Product Characteristics" © Jan. 2001 DSM Engineering Plastics, Jan. 2001, 6 pages.

Brochure—"DuPont Hytrel Polyester Elastomer Product and Properties Guide" dated on or before Jun. 23, 2004, 12 pages.

Chapter 7 and Chapter 10, Introduction to Magnetic Properties, *Electrical and Magnetic Properties of Metals*, ASM International®, printed on or before May 16, 2002, pp. 193-195 and 263-270.

Kolobow et al., "A New Thin-Walled Nonkinking Catheter for Peripheral Vascular Cannulation," Surgery, vol. 68, No. 4, Oct. 1970, pp. 625-629.

Schröder, Chris, "New Developments in Co-polyester Based thermoplastic Elastomers," Source Unknown, dated on or before Jun. 23, 2004, 5 pages.

Schueler, Beth A. et al., "MRI Compatibility and Visibility Assessment of Implantable Medical Devices," *Journal of Magnetic Resonance Imaging*, vol. 9. (1999) pp. 596-603.

Spees, William M. et al., "Water Proton MR Properties of Human Blood at 1.5 Tesla: Magnetic Susceptibility, $T_1$, T, $T^*_2$, and Non-Lorentzian Signal Behavior," *Magnetic Resonance in Medicine*, vol. 45 (2001) pp. 533-542.

Teweldemedhin, Z.S. et al., "Magnetic Susceptibility Measurements of Solids," source unknown, dated on or before Jan. 6, 2000, 8 pages.

\* cited by examiner

MEDICAL DEVICE INCORPORATING A POLYMER BLEND

CROSS-REFERENCE TO RELATED APPLICATIONS

This application is a continuation of co-pending U.S. patent application Ser. No. 10/875,108, filed Jun. 23, 2004, which is a continuation-in-part of co-pending U.S. patent application Ser. No. 10/645,764, filed Aug. 20, 2003, the entire disclosures of which are incorporated herein by reference.

TECHNICAL FIELD

The invention relates generally to elongate medical devices and more particularly to catheters and catheter shafts that include improved polymer blends and/or braided or other reinforcement elements.

BACKGROUND OF THE INVENTION

Reinforcing layers such as reinforcing braid layers can provide thin-walled catheters with desired resistance to kinking while retaining desirable flexibility. In some instances, it can be desirable for portions of a thin-walled catheter to be either more flexible or less flexible than other portions of the catheter. In particular, it can be desirable for a distal portion of a catheter to be more flexible, especially if the distal portion of the catheter is curved. However, a reinforcing braid layer that can provide suitable kink resistance in other portions of a catheter may not provide sufficient flexibility in the distal portion of the catheter.

A need remains for improved catheters having desirable kink resistance while being sufficiently flexible, particularly in distal portions that can be curved in use, especially when tracking dramatic bends in the vasculature of an individual.

SUMMARY OF THE INVENTION

The present invention is directed to catheters, catheter shafts, and methods for making and using the same. In some embodiments, the catheters may include a polymer blend. For example, the blend may include polyoxymethylene added in the dispersion phase to a polymer blend.

The catheters and catheter shafts can also include a braid that can be woven from continuous wires in some embodiments. A portion of each wire can have a diameter that is reduced with respect to another portion of that wire. Accordingly, an exemplary embodiment of the invention can be found in a catheter braid that is formed from at least two continuous wires that are woven together. The catheter braid can include a proximal braid section in which each of the continuous wires have a proximal diameter, and a distal braid section in which each of the continuous wires have a distal diameter. For each continuous wire, in one preferred embodiment, the distal diameter of the continuous wire is less than the proximal diameter of the continuous wire.

Another example embodiment of the invention can be found in a catheter that has a distal end and a proximal end, and a distal region that is proximate the distal end. The catheter can include an inner layer that extends from the distal end to the proximal end, and a reinforcing braid layer that can be disposed over the inner layer. The braid layer can be formed from at least two continuous wires that are woven together. The braid layer can have a proximal braid section in which each of the continuous wires has a proximal diameter, and a distal braid section in which each of the continuous wires has a distal diameter. The distal diameter of each continuous wire, in one preferred embodiment, is less than the proximal diameter of each continuous wire.

An example embodiment of the invention can also be found in a method of forming a catheter that has a distal end and a proximal end. The catheter can include an inner layer and a braid layer. The catheter can be formed by weaving together at least two continuous wires to form the braid layer. The formed braid layer distal portion is then, in a preferred embodiment, immersed in an etching solution to thin the wires to a desired reduced diameter. The resulting braid layer has a proximal section in which each of the wires has a proximal diameter and a distal section in which each of the wires has a distal diameter that is less than the proximal diameter. The braid layer, once formed, can be positioned over the inner layer.

DETAILED DESCRIPTION OF THE PREFERRED EMBODIMENTS

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

Figure 1:
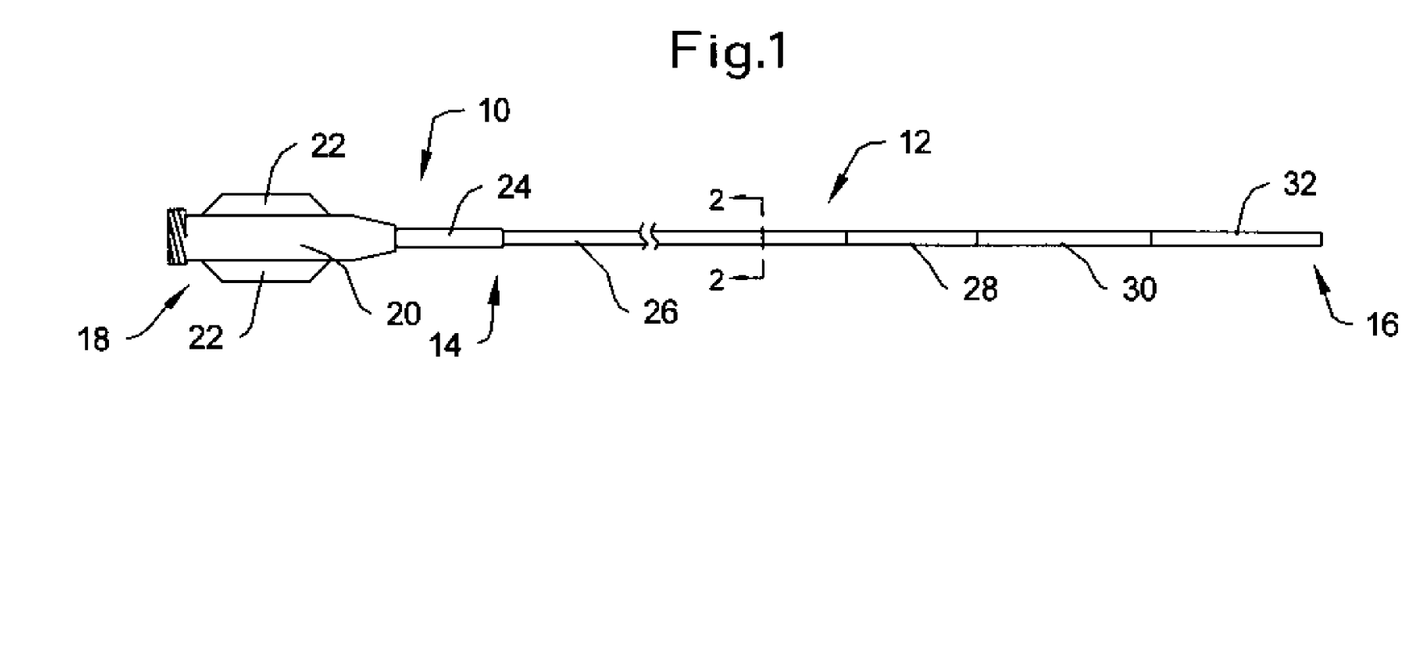
FIG. 1 is a plan view of a catheter in accordance with an embodiment of the invention.

FIG. 1 is a plan view of a catheter 10 in accordance with an embodiment of the invention. The catheter 10 can be any of a variety of different catheters. In some embodiments, the catheter 10 can be an intravascular catheter. Examples of intravascular catheters include balloon catheters, atherectomy catheters, drug delivery catheters, diagnostic catheters and guide catheters. The intravascular catheter 10 can be sized in accordance with its intended use. The catheter 10 can have a length that is in the range of about 50 to about 150 centimeters, preferably in the range of about 100 to about 150 centimeters, and can have any useful diameter. As illustrated, FIG. 1 portrays a guide catheter, but the invention is not limited to such. Preferred methods of manufacture are described herein. The catheter 10 can also be manufactured using conventional techniques.

In the illustrated embodiment, the intravascular catheter 10 includes an elongate shaft 12 that has a proximal end 14 and a distal end 16. A hub and strain relief assembly 18 can be connected to the proximal end 14 of the elongate shaft 12. The hub and strain relief assembly 18 includes a main body portion 20, and a strain relief 24 that is intended to reduce kinking. The hub can also include a pair of flanges 22. The hub and strain relief assembly 18 can be of conventional design and can be attached using conventional techniques.

The elongate shaft 12 can include one or more shaft segments having varying degrees of flexibility. As illustrated, the elongate shaft 12 includes a first shaft segment 26, a second shaft segment 28 and a third shaft segment 30. In some embodiments, the elongate shaft 12 can include fewer shaft segments or only one shaft segment or can include more than three segments, depending on the flexibility requirements of a particular application.

Figure 2:
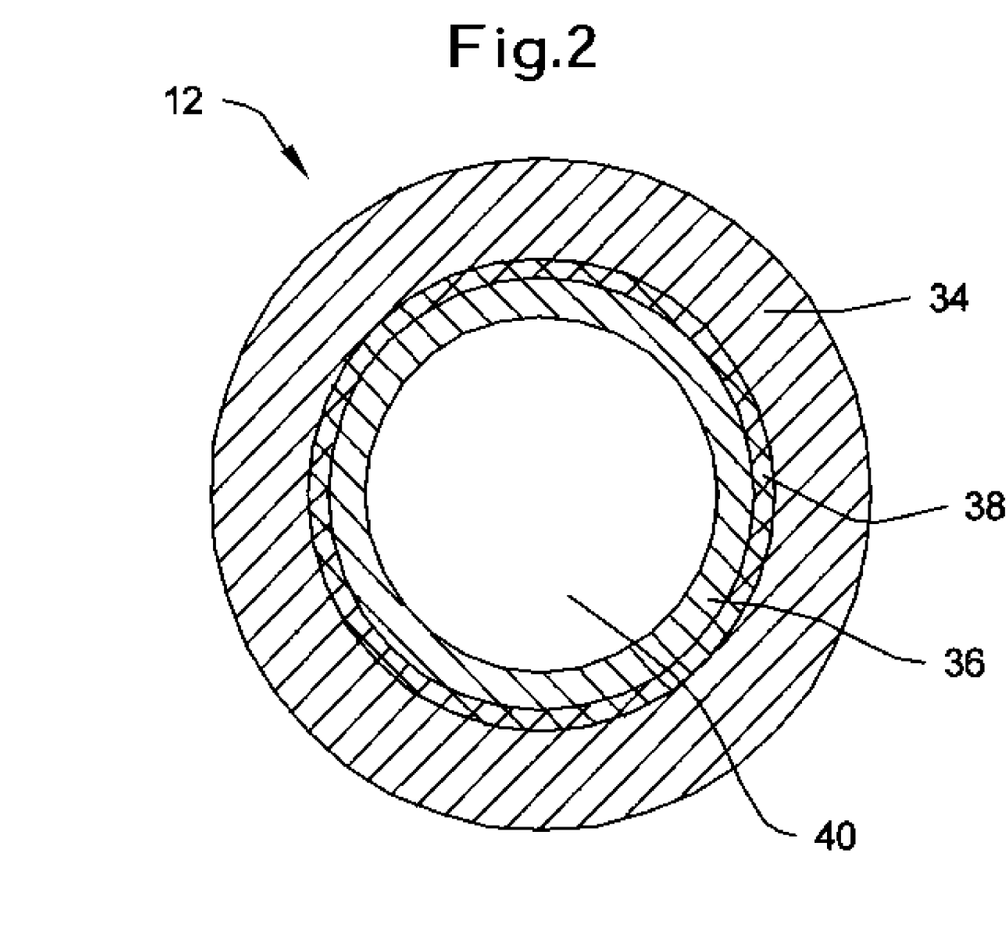
FIG. 2 is a cross-sectional view of the catheter of FIG. 1 taken along line 2-2.
Figure 3:
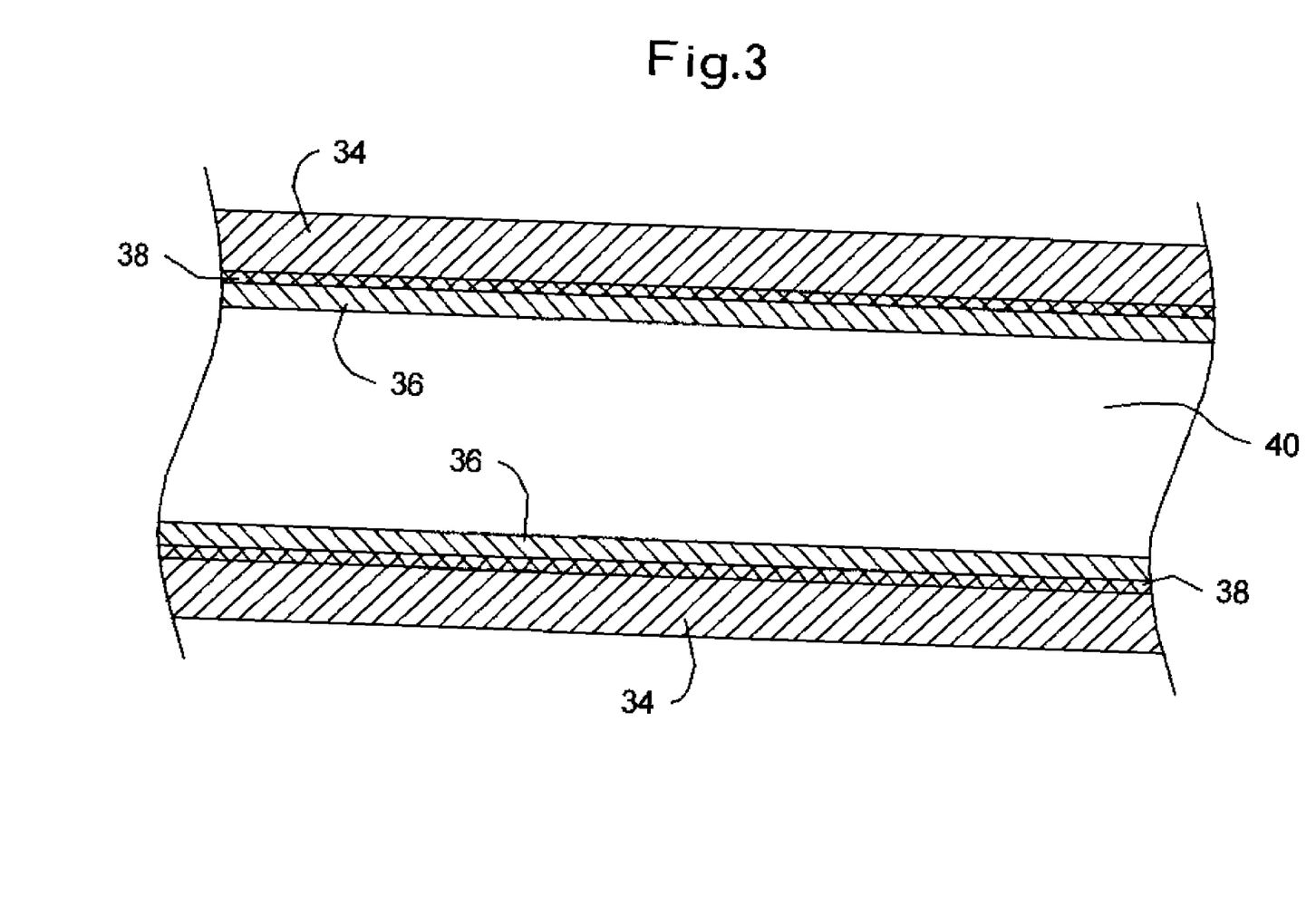
FIG. 3 is a partially sectioned view of the catheter of FIG. 1.

FIG. 2 is a cross-sectional view of the elongate shaft 12, taken along the line 2-2 of FIG. 1, while FIG. 3 is a longitudinal cross-sectional view of a portion of the elongate shaft 12. The proximal portions of the elongate shaft 12, as illustrated, include an outer layer 34 and an inner layer 36, and can include a reinforcement layer 38 that is positioned between the inner layer 36 and the outer layer 34. The inner layer 36 defines a lumen 40 that extends through the elongate shaft 12. The distal portion 32 of the elongate shaft 12 will be discussed in greater detail hereinafter.

Each of the shaft segments 26, 28, 30 can have a similar construction. In particular, each of the shaft segments 26, 28, 30 can include an inner layer 36, a reinforcing layer 38 that is the same for or continuous through each of the shaft segments 26, 28, 30 and an outer layer 34 that becomes more flexible in the shaft segments 26, 28, 30 closest to the distal end 16 of the catheter 10. For example, the proximal shaft segment 26 can have an outer layer that is formed from a polymer having a hardness of 72D (Durometer), the intermediate shaft segment 28 can have an outer layer having a hardness of 68D and the distal shaft segment 30 can have an outer layer having a hardness of 46D.

Each of the shaft segments 26, 28, 30 can be sized in accordance with the intended function of the resulting catheter 10. For example, the shaft segment 26 can have a length of about 35 inches, the shaft segment 28 can have a length in the range of about 2 to 3 inches and the shaft segment 30 can have a length in the range of about 1 to 1.25 inches.

The shaft segments 26, 28, 30 can be formed of any suitable material such as a polymeric material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or polyester elastomers such as HYTREL® available from DuPont), polyamide (for example, DURETHAN® available from Bayer or CRISTA-MID® available from Elf Atochem), elastomeric polyamides, block polyamide/ethers, polyether block amide (PEBA, for example available under the trade name PEBAX®), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments, any one or all of shaft segments 26, 28, 30 can be blended with a liquid crystal polymer (LCP). For example, the mixture can contain up to about 6% LCP. This has been found to enhance torqueability.

In these and some other embodiments, any one or all of shaft segments 26, 28, 30 can include polymer blends. Some examples of suitable polymer blends include PBT and polyether-ester blends (e.g., PBT/ARNITEL®), PBT and ether or ester based copolymer blends (e.g., PBT/HYTREL® blends), POM combined with a PBT and polyether-ester blend (e.g., DELRIN®, PBT, and ARNITEL®), POM combined with a PBT and ether or ester based copolymer blend (e.g., DELRIN®, PBT, and HYTREL® blends), other polyesters (such as polyethylene terephthalate (PET), polytrimethylene terephthalate, polyethylene naphthalate (PEN)) blended with polyether-ester, other polyesters blended with ether or ester based copolymer, POM combined with other polyesters blended with polyether-ester, POM combined with other polyesters blended with ether or ester based copolymer, polyurethane and POM blends, and the like or any other suitable blend. In general, as the amount of POM added increases, the strength of the resultant blend increases. Some example volume percents for blends including POM, PBT, and ether or ester based copolymer such as HYTREL® (or a polyether-ester such as ARNITEL®) suitable for making any one or all of the shaft segments 26, 28, 30 are listed in Table 1 below.

TABLE 1

| POM | PBT | ether or ester based copolymer (e.g., HYTREL ®) or polyether-ester (e.g., ARNITEL ®) |
| --- | --- | --- |
| 5% | 55% | 40% |
| 10% | 50% | 40% |
| 20% | 40% | 40% |
| 30% | 30% | 40% |
| 40% | 20% | 40% |
| 30% | 40% | 30% |
| 30% | 50% | 20% |
| 30% | 60% | 10% |

Other volume percents are contemplated. For example, some blends may include about 5% to about 90% PBT or about 5% to about 90% ether or ester based copolymer (e.g., HYTREL®) or polyether-ester (e.g., ARNITEL®).

Polymer blends such as PBT/polyether-ester and PBT/ether or ester based copolymer (for example, PBT/ARNITEL® and PBT/HYTREL®) are useful for making catheter shafts such as shaft 12 as well as any other medical device that includes a polymeric structure. One reason that these blends are desirable is because of its ease in manufacturing, for example, processes such as extrusion. Adding POM to these blends may be desirable because the POM allows for stronger yet more flexible shafts to be manufactured due to the properties of POM. Typical POM blends, however, are not as easy to extrude as PBT/ARNITEL® and PBT/HYTREL®. It has been determined that adding POM in the dispersion phase to PBT/ARNITEL® or PBT/HYTREL® blends allows shafts to be manufactured (e.g., shaft 12) that have the desirable characteristics of POM (e.g., strength and flexibility) while still having the ease in manufacturing of PBT/ARNITEL® or PBT/HYTREL® blends. Accordingly, using a blend that combines POM in the dispersion phase with a PBT/ARNITEL® or PBT/HYTREL® blend allows shaft 12 to be manufactured with the desired amount of strength and flexibility, even when shaft 12 has a relatively low profile, is thin-walled, or otherwise reduced in size.

Dispersing or otherwise adding POM in the dispersion phase is understood to be dispersing POM in a molten PBT/ARNITEL® or PBT/HYTREL® blend. Alternatively, all three materials (i.e., POM/PBT/ARNITEL® or POM/PBT/HYTREL®) can be melted at the same time. Because adding POM in the dispersion phase will occur at temperature where the PBT/ARNITEL® or PBT/HYTREL® blend is melted and because the melting temperature of PBT/ARNITEL® and PBT/HYTREL® blends are higher than POM, the POM will also melt when added in the dispersion phase. However, the POM will not mix with the PBT/ARNITEL® or PBT/HYTREL® blend. Instead, the particles of molten POM will disperse in the melted PBT/ARNITEL® or PBT/HYTREL® blend. In a sense, the dispersion phase POM together with PBT/ARNITEL® or PBT/HYTREL® blend would be similar in appearance to an oil and water mix (i.e., the POM being akin to the "oil" and the PBT/ARNITEL® or PBT/HYTREL® blend being akin to the "water"). It should be noted that the amount of POM that can be added in the dispersion phase appears to be limited. For example, blends with about 50% or more POM tend to not disperse as well in PBT/ARNITEL® or PBT/HYTREL® blends. In some instances, increasing the amount of POM can result in the opposite phenomenon, i.e., the PBT/ARNITEL® or PBT/HYTREL® blend "dispersed" in the POM.

In some embodiments, adding POM in the dispersion phase may occur prior to or during an extrusion process, for example, an extrusion process suitable for manufacturing shaft 12, any or all of shaft segments 26/28/30, or any other portion of catheter 10. Thus, the molten PBT/ARNITEL® or PBT/HYTREL® blend having POM added in the dispersion phase would be extruded to form shaft 12 or any of segments 26, 28, 30. As stated above, the POM will not directly mix with the PBT/ARNITEL® or PBT/HYTREL® blend when dispersed or combined in the dispersion phase. Instead, the POM will remain as a series of particles or droplets dispersed in the PBT/ARNITEL® or PBT/HYTREL® blend. Moreover, the resultant shaft 12 will have a material composition where the POM remains dispersed in the PBT/ARNITEL® or PBT/HYTREL® blend.

Adding POM in the dispersion phase may be desirable for a number of reasons. For example, adding POM in the dispersion phase to the PBT/ARNITEL® or PBT/HYTREL® blend allows for greater flexibility in terms of adjusting the performance of the resultant shafts 12. This may make it easier, for example, to adjust the amounts of POM in the polymer blend than if the POM was blended in some other manner. In addition, by adding POM in the dispersion phase together with the PBT/ARNITEL® or PBT/HYTREL® blend, the combination is more easily extruded than other polymer blends that include POM not in the dispersion phase. These same desirable characteristics can also be realized with other combinations of dispersion phase POM and polymer blends including any of those combinations listed above. For example, dispersion phase POM can be added to PBT/ARNITEL® or PBT/HYTREL® blend.

Once the shaft 12 or shaft segments 26, 28, 30 are extruded, they may be subjected to one or more curving processes and/or other processes that include heating typically used in catheter 10 manufacturing. The curving processes may include disposing shaft 12 in a mold corresponding to the desired final curve and then heating. In some embodiments, the heating may occur at a temperature at or near the highest temperature possible that will not melt the PBT/ARNITEL® or PBT/HYTREL® blend. For example, the heating may take place at a temperature higher than the melting point of POM but lower than the melting point of the PBT/ARNITEL® or PBT/HYTREL® blend. However, a number of other temperatures and manufacturing conditions are contemplated and known in the art.

In some embodiments, the inner layer 36 can be a single piece uniform material extending over the length of the shaft 12 and can define a lumen 40 that can run the entire length of the elongate shaft 12 and that is in fluid communication with a lumen (not illustrated) extending through the hub assembly 18. The lumen 40 defined by the inner layer 36 can provide passage to a variety of different medical devices or fluids, and thus the inner layer 36 can be manufactured from or include a lubricious material to reduce friction within the lumen 40. Examples of suitable materials include polytetrafluoroethylene (PTFE), such as TEFLON®. The inner layer 36 can be dimensioned to define a lumen 40 having an appropriate inner diameter to accommodate its intended use. In some embodiments, the inner layer 36 can define a lumen 40 having a diameter in the range of about 0.04 to about 0.10 inches and can have a wall thickness of about 0.001 to about 0.02 inches.

In some embodiments, the outer layer 34 can include a portion made from a thermoplastic polymer such as a co-polyester thermoplastic polymer such as that available commercially under the ARNITEL® name. The use of an ARNITEL® polymer is described in detail below. The outer layer 34 can have an inner diameter that is about equal to the outer diameter of the inner layer 36. The outer layer 34 can have an inner diameter that is slightly greater than the outer diameter of the inner layer 36 to accommodate the thickness of the reinforcing braid layer 38. In some embodiments, the outer layer 34 can have an inner diameter in the range of about 0.0600 to about 0.0618 inches and an outer diameter in the range of about 0.0675 to about 0.0690 inches.

In some embodiments, the outer layer 34 or portions thereof can include or be filled with a radiopaque material to make the outer layer 34 or portions thereof more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the polymer can include different sections having different amounts of loading with radiopaque material. For example, the outer layer 34 can include a distal section having a higher level of radiopaque material loading, and a proximal section having a correspondingly lower level of loading.

A reinforcing braid layer 38 can be positioned between the inner layer 36 and the outer layer 34. The reinforcing braid layer 38 can be formed of any suitable material, including metals and metal alloys. In some embodiments, the reinforcing braid layer 38 can include a metal wire braid (with wires that are round, flat, or other cross-sectional shape) formed of stainless steel, tungsten, gold, titanium, silver, copper, platinum, or iridium. The reinforcing braid layer 38 can also be formed from non-metallic material such as KEVLAR® (poly paraphenylene terephthalamide) fibers, LCP (liquid crystal polymer) fibers or glass fibers. In some embodiments, the reinforcing braid layer 38 can be formed of a high tensile stainless steel such as 304V stainless steel. In still other embodiments, the reinforcing braid layer 38 can be formed of a polymeric material or polymer blend such as any those disclosed herein.

In some embodiments, the reinforcing braid layer 38 can extend over substantially the entire length of the catheter 10. The reinforcing braid layer 38 can extend from a position proximate to or distal of the proximal end 14 of the elongate shaft 12 to a position proximate to or proximal of the distal end 16 of the elongate shaft 12.

Figure 4:
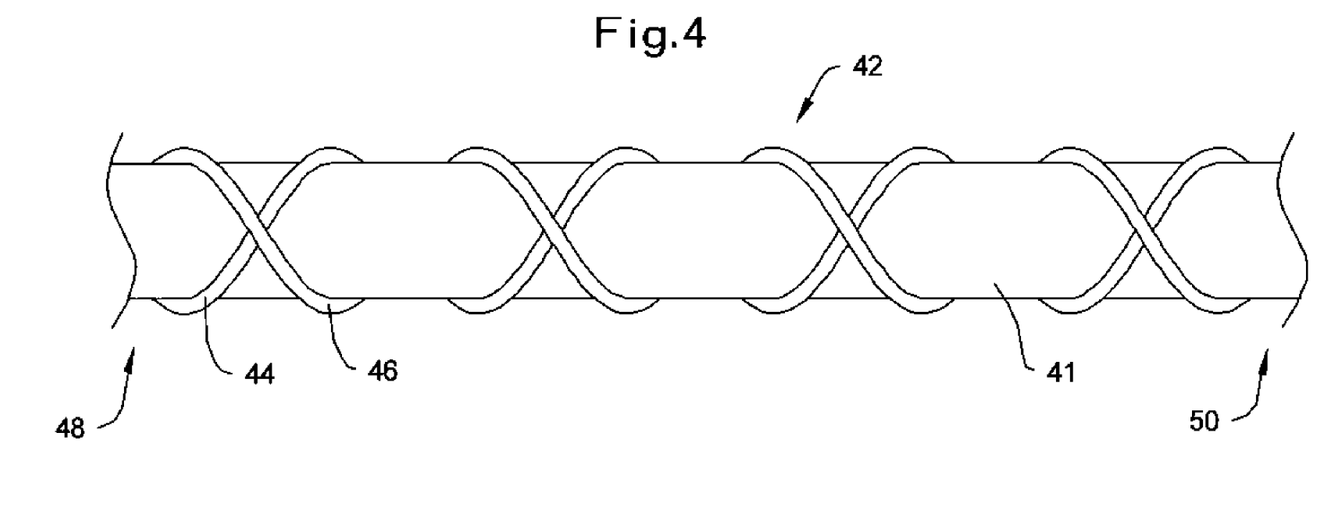
FIG. 4 is a partially sectioned cutaway view of a portion of a woven braid in accordance with an embodiment of the invention.

As illustrated, for example, in FIG. 4, a reinforcing braid 42 can be formed of several continuous fibers. In some embodiments, the reinforcing braid 42 can be formed by weaving together two or more continuous wires over a mandrel 41. The continuous wires can be flat or round in cross-section and can be woven together in a variety of patterns. The reinforcing braid 42 can be formed by weaving together two continuous wires 44 and 46, as illustrated.

However, the invention contemplates, for example, using three continuous wires woven together in a three-over-three pattern, while other patterns such as a four-over-four, two-over-four, or even a five-over-five pattern can also be used, depending on the number of wires used. In particular, the wires can have a round cross section having a diameter of about 1.0 to about 2.0 millimeters. The braid can also be formed with flat or other non-round cross sections. If such a braid is used, the cross section reduces in dimension, such as width and height, versus diameter for a round wire.

A reinforcing braid 42 can be formed by weaving together two continuous wires 44 and 46 that have cross-sectional diameters that are at least substantially constant from a proximal end 48 of the reinforcing braid 42 to a distal end 50 of the reinforcing braid 42. As used herein, a continuous wire is a single wire that extends from one end of the braid to the other end of the braid, without splicing, welding or any other means of joining two wires together. A continuous wire can have a constant diameter across its entire length. A continuous wire can have a diameter that changes along its length. The diameter can vary continuously, or the diameter can vary stepwise.

In some embodiments, each of the continuous wires 44, 46 can have the same diameter. In other embodiments, not illustrated, it is contemplated that one continuous wire 44 can have a first constant diameter, while the second continuous wire 46 has a second constant diameter that is either greater or less than the first constant diameter.

Forming a braid 42 from continuous wires 44, 46 of constant diameter can produce a braid 42 having uniform flexibility, torque transmission and other useful performance parameters. In some embodiments, a braid 42 as illustrated in FIG. 4 can be used in part or all of a catheter 10 and forms the reinforcing braid layer 38 illustrated in the earlier Figures. In some embodiments, the braid 42 can extend from the proximal end 14 of the elongate shaft 12 to a point proximal of the distal end 16 of the elongate shaft 12.

Figure 6:
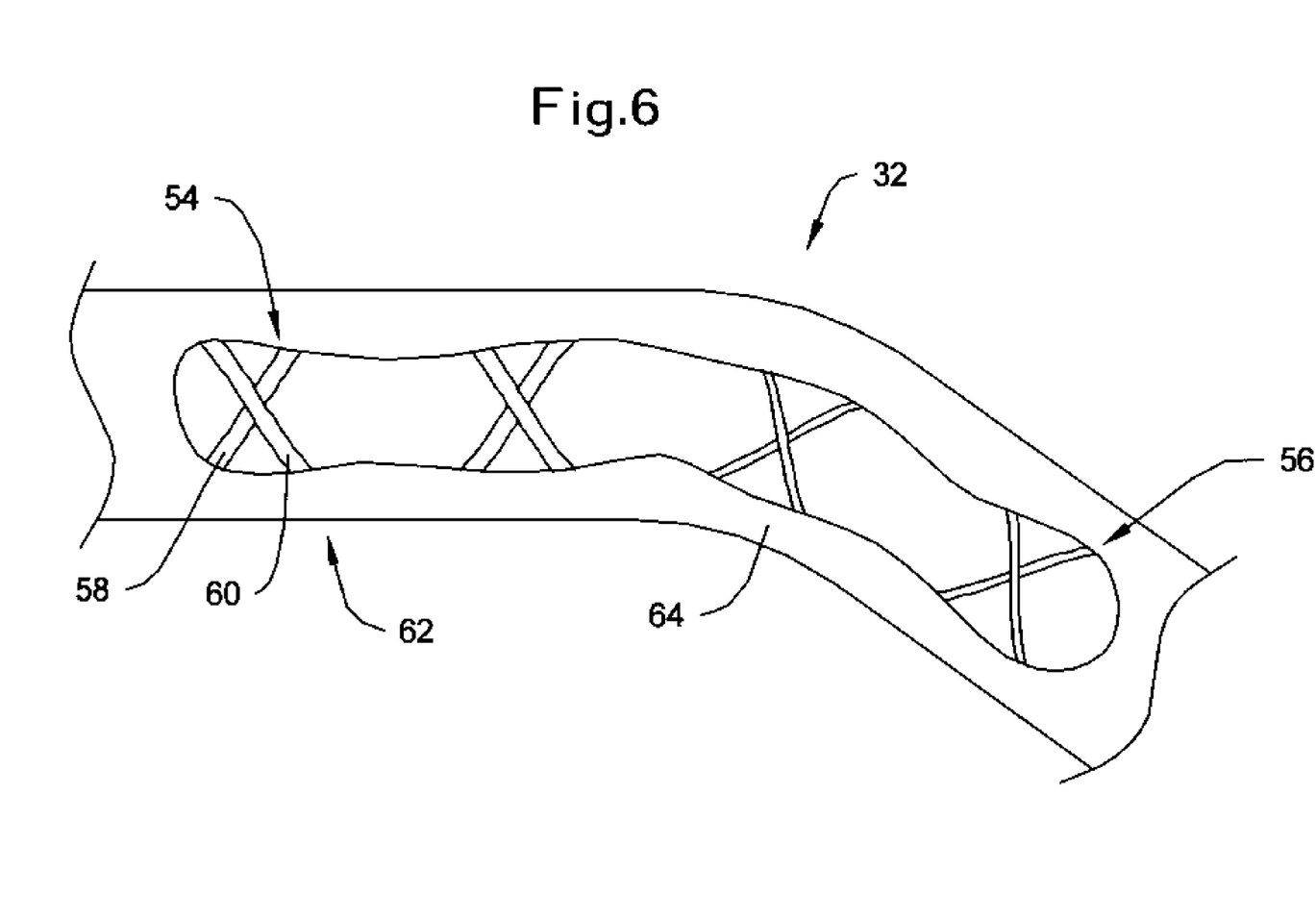
FIG. 6 is a partially sectioned view of a distal portion of the catheter of FIG. 1.

In some embodiments, it can be desirable for a portion of the braid 42 to be more flexible than another portion of the braid 42. It may be useful for the distal portion 50 of the braid 42 to be more flexible than the proximal portion 48. For example, catheters can have a distal portion 32 that can be curved, as indicated in FIG. 6. In some embodiments, the distal portion 32 can curve in response to anatomical features encountered in use. In other embodiments, the distal portion 32 can be pre-bent or pre-curved prior to use. In order to more easily curve, it can be useful for any braid present in the distal portion 32 to be more flexible.

Figure 5:
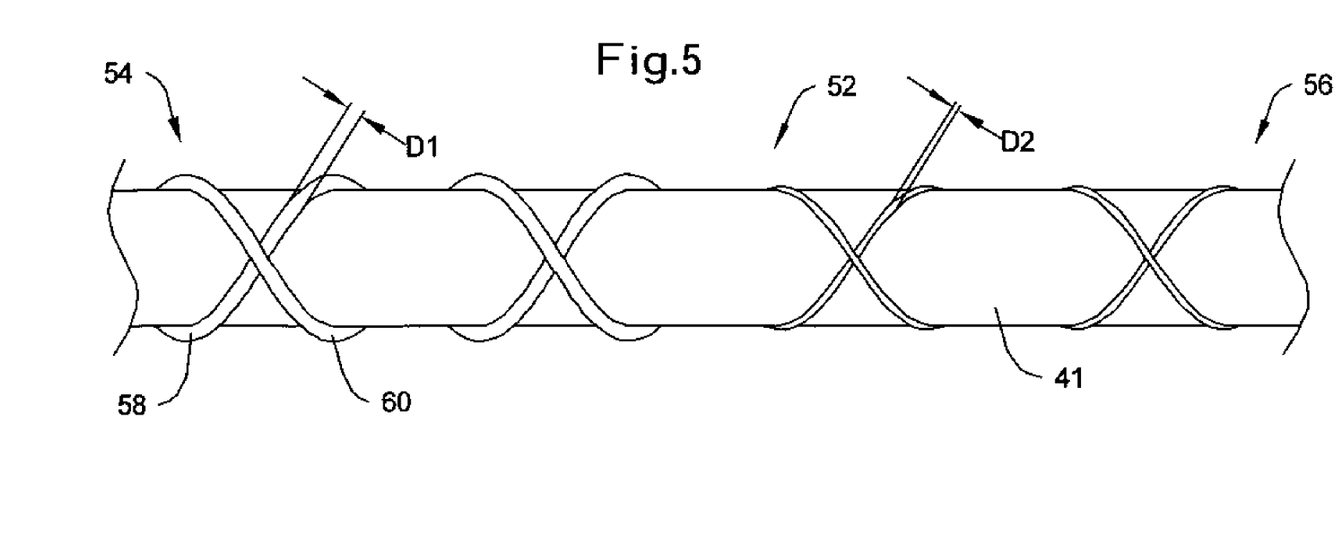
FIG. 5 is a partially-sectioned view of a portion of a woven braid in accordance with an embodiment of the invention.

FIG. 5 illustrates an embodiment of a reinforcing braid 52 that can be formed, as described above with respect to FIG. 4, by weaving together two or more continuous wires 58 and 60 over a mandrel 41. The braid 52 shown in FIG. 5 has a proximal portion 54 in which each of the continuous wires 58, 60 has a proximal diameter D1 and a distal portion 56 in which each of the continuous wires 58, 60 has a distal diameter D2.

The illustrated embodiment, the distal diameter D2 is less than the proximal diameter D1. In some embodiments, the distal diameter D2 can be about one-third less than the proximal diameter D1. In a particular embodiment, the proximal diameter D1 can be about 1.5 millimeters, while the distal diameter D2 is about 1.0 millimeters. The use of diameter is illustrative of a round wire, although other shaped wire can be used with commensurate change in cross-sectional area.

As can be seen in FIG. 6, the reinforcing braid 52 can be positioned within a catheter portion 32 such that the proximal portion 54 of the braid corresponds to a more proximal section 62 of the catheter portion 32, while the distal portion 56 of the braid 52 corresponds to a curved, more distal section 64 of the catheter portion 32. As a result, the catheter portion 32 can be more flexible and supportive. In some embodiments, the reinforcing braid 52 can extend proximally to the proximal end 14 of the elongate shaft 12. In such embodiments, the proximal portion 54 forms the reinforcing braid layer 38.

The reinforcing braid 52 shown in FIG. 6 can be formed in a variety of ways. In some embodiments, the braid 52 can be formed from two continuous wires 58, 60, each having equal, constant diameters. The distal portion 56 of the braid 52 can then be subjected to a procedure that will reduce the diameter of the wires 58, 60 within the distal portion 56 of the braid 52. A number of procedures are contemplated, although electro-etching is preferred.

In other embodiments, the braid 52 can be formed from two continuous wires 58, 60 that do not have constant diameters. In particular, each of the two continuous wires 58, 60 can be formed having a first portion having a first diameter and a second portion having a second, reduced diameter. The first diameter can correspond to the proximal diameter of the continuous wires 58, 60, while the second diameter can correspond to the distal diameter of the continuous wires 58, 60. The continuous wires 58, 60 can have a gradual transition between the first and second diameters. The wires 58, 60 can also be formed having a more abrupt transition between the first and second diameters. The wires 58, 60 can be formed using any of a variety of procedures, although cold-drawing is preferred.

Once the braid 52 has been formed, it can be incorporated into a catheter 10. An inner layer 36 can be placed on a mandrel. The braid 52 can be positioned over the inner layer 36 by axially compressing the braid 52. This enlarges the inner diameter of the braid 52 and permits easy positioning of the braid 52 over the inner layer 36. Once the braid 52 has been positioned to form the reinforcing braid layer 38, an outer layer 34 can be installed if desired. The outer layer 34 can be co-extruded over the reinforcing braid layer 38, or it can be preformed and then heat shrunk into position.

In at least some embodiments, portions or all of the reinforcing braid layer 38 can include a radiopaque material. Some examples of radiopaque materials can include, but are not limited to, gold, platinum, palladium, tantalum, tungsten or tungsten alloy, molybdenum, polymer material loaded with a radiopaque filler, and the like.

In some embodiments, a degree of MI compatibility can be imparted. For example, to enhance compatibility with Magnetic Resonance Imaging (MRI) machines, it may be desirable to make the reinforcing braid layer 38, or other portions thereof, in a manner that would impart a degree of MRI compatibility. For example, the reinforcing braid layer 38 or portions thereof may be made of a material that does not substantially distort the image and create substantial artifacts, which are gaps in the image. Certain ferromagnetic materials, for example, may not be suitable because they may create artifacts in an MRI image. The reinforcing braid layer 38 or portions thereof may also be made from a material that the MRI machine can image. Some materials that exhibit these characteristics include, for example, tungsten, Elgiloy, MP35N, nitinol, and the like, and others.

An intravascular catheter 10 can optionally include a coating layer such as a lubricious coating layer over part or all of the catheter 10. Suitable lubricious polymers are well known in the art and can include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What I claim is:

1. A method for manufacturing a catheter shaft, comprising the steps of:
   providing a molten blend of polybutylene terephthalate and ether or ester based copolymer;
   adding polyoxymethylene in the dispersion phase to the molten blend of polybutylene terephthalate and ether or ester based copolymer to define a polymer blend; and
   extruding a shaft member from the polymer blend.

2. The method of claim 1, wherein the polymer blend includes about 5% to about 40% by volume of polyoxymethylene.

3. The method of claim 2, wherein the polymer blend includes about 5% to about 90% by volume polybutylene terephthalate.

4. The method of claim 2, wherein the polymer blend includes about 5% to about 90% by volume ether or ester based copolymer.

5. The method of claim 1, wherein the molten blend of polybutylene terephthalate and ether or ester based copolymer includes polyether-ester.

6. The method of claim 1, further comprising disposing a braid on the shaft member.

7. The method of claim 6, wherein the braid has a proximal portion and a distal portion different from the proximal portion.

8. The method of claim 6, wherein the braid is formed from at least two continuous wires woven together.

9. The method of claim 8, wherein the braid includes a proximal braid section in which each of the continuous wires has a proximal cross-sectional area and a distal braid section in which each of the continuous wires has a distal cross-sectional area, and wherein for each continuous wire, the distal cross-sectional area is less than the proximal cross-sectional area.

* * * * *

UNITED STATES PATENT AND TRADEMARK OFFICE
CERTIFICATE OF CORRECTION

| | | |
|---|---|---|
| PATENT NO. | : 8,251,976 B2 | |
| APPLICATION NO. | : 12/606488 | |
| DATED | : August 28, 2012 | |
| INVENTOR(S) | : Pu Zhou | |

It is certified that error appears in the above-identified patent and that said Letters Patent is hereby corrected as shown below:

In the Specifications:

Column 4
Lines 64 - 65: delete "PBTIARNITEL" and insert therefor -- PBI/ARNITEL --.

Column 8
Line 15: delete "The illustrated" and insert therefor -- In the illustrated --.

Column 9
Line 4: delete "MI" and insert therefor -- MRI --.

Signed and Sealed this
Eighth Day of January, 2013

David J. Kappos
*Director of the United States Patent and Trademark Office*